US009026374B2

(12) United States Patent
Andersson et al.

(10) Patent No.: US 9,026,374 B2
(45) Date of Patent: May 5, 2015

(54) METHOD AND DEVICE FOR DETERMINING THE RELATIVE HUMIDITY OF AN INSULATING LIQUID FILLED ELECTRIC APPARATUS

(75) Inventors: Gunnar Andersson, Nyhammar (SE); Bengt-Olof Stenestam, Ludvika (SE)

(73) Assignee: ABB Technology Ltd. (CH)

( * ) Notice: Subject to any disclaimer, the term of this patent is extended or adjusted under 35 U.S.C. 154(b) by 1101 days.

(21) Appl. No.: 12/914,718

(22) Filed: Oct. 28, 2010

(65) Prior Publication Data

US 2011/0093216 A1   Apr. 21, 2011

Related U.S. Application Data

(63) Continuation of application No. PCT/EP2009/053150, filed on Mar. 17, 2009.

(30) Foreign Application Priority Data

Apr. 28, 2008   (EP) ..................... 08155250

(51) Int. Cl.
  *G01N 33/00*   (2006.01)
  *H01H 19/00*   (2006.01)
  (Continued)

(52) U.S. Cl.
  CPC ............ *H01F 27/14* (2013.01); *G01N 33/0031* (2013.01); *G01N 33/2847* (2013.01); *H01F 27/402* (2013.01); *H01F 2027/404* (2013.01)

(58) Field of Classification Search
  CPC . G01N 33/2847; G01N 25/56; G01N 27/048; G01N 27/121; G01N 27/223; G01N 27/423; G01N 33/0016; H01F 27/14; H01F 27/402; H01F 2027/404
  USPC ....... 702/24, 50; 55/434.2; 73/73; 200/11 TC
  See application file for complete search history.

(56) References Cited

U.S. PATENT DOCUMENTS 4,212,194 A * 7/1980 Allen et al. ................. 73/73
7,332,015 B2 * 2/2008 Golner et al. ............... 95/10
(Continued)

FOREIGN PATENT DOCUMENTS

KR   1020060126534 A   12/2006
RU       2263989 C2    11/2005
(Continued)

OTHER PUBLICATIONS

European Search Report; Application No. EP 08 15 5250; Sep. 10, 2008; 6 pages.
(Continued)

*Primary Examiner* — Michael Nghiem
*Assistant Examiner* — Eman Alkafawi
(74) *Attorney, Agent, or Firm* — St. Onge Steward Johnston & Reens LLC

(57) ABSTRACT

A method for determining the relative humidity of an insulating liquid filled electric apparatus including a container containing insulating liquid and gas, a communication unit providing communication between the gas of the container and gas of an external environment, and providing dehydration of gas passing through the communication unit, wherein the method includes: continuously measuring and storing the relative humidity of the gas in the container, calculating an average value of the relative humidity in the gas based on the stored humidity measurements during a certain time period, and determining the relative humidity of the insulating liquid based on the average value of the relative humidity in the gas and a relationship between the relative humidity of the gas and the relative humidity of the insulating liquid at equilibrium.

12 Claims, 3 Drawing Sheets

(51) Int. Cl.
*H01F 27/14* (2006.01)
*G01N 33/28* (2006.01)
*H01F 27/40* (2006.01)

(56) References Cited

U.S. PATENT DOCUMENTS

| | | | |
|---|---|---|---|
| 2004/0021449 A1* | 2/2004 | Stenestam et al. | 323/255 |
| 2005/0103195 A1* | 5/2005 | Golner | 96/111 |
| 2006/0162304 A1* | 7/2006 | Eichert et al. | 55/434.2 |
| 2006/0201247 A1* | 9/2006 | Speldrich et al. | 73/335.06 |
| 2007/0199443 A1* | 8/2007 | Viereck et al. | 95/10 |
| 2007/0289367 A1 | 12/2007 | Aubin et al. | |
| 2008/0198569 A1* | 8/2008 | Findeisen | 361/837 |
| 2013/0340500 A1* | 12/2013 | Miller et al. | 73/29.02 |

FOREIGN PATENT DOCUMENTS

| | | |
|---|---|---|
| SU | 1003161 A1 | 3/1983 |
| SU | 1145380 A1 | 3/1985 |
| WO | 2006069360 A2 | 6/2006 |

OTHER PUBLICATIONS

Kaufman, et al.; "Gas and Moisture Equilibriums in the Transformer Oil"; Transactions of the American Institute of Electrical Engineers; vol. 74, No. 19, Jul. 1955; 8 pages.

International Search Report and Written Opinion of the International Searching Authority; PCT/EP2009/053150; Jun. 19, 2009; 12 pages.

Oommen T. V.; "On-Line Moisture Sensing in Transformers"; Electrical Electronics Insulation Conference; Oct. 7, 1991; 6 pages.

\* cited by examiner

METHOD AND DEVICE FOR DETERMINING THE RELATIVE HUMIDITY OF AN INSULATING LIQUID FILLED ELECTRIC APPARATUS

CROSS-REFERENCE TO RELATED APPLICATIONS

The present application is a continuation of pending International patent application PCT/EP2009/053150 filed on Mar. 17, 2009 which designates the United States and claims priority from European Patent application 08155250.7 filed on Apr. 28, 2008, the content of which is incorporated by reference.

FIELD OF THE INVENTION

The present invention relates to a method and a device for determining the relative humidity of an insulating liquid filled electric apparatus comprising a container containing insulating liquid and gas, a communication unit providing communication between the gas of the container and gas of an external environment, and providing dehydration of gas passing through the communication unit.

BACKGROUND OF THE INVENTION

An insulating liquid filled electric apparatus, such as a transformer, a tap changer or switchgear, is an apparatus used in application where isolation and cooling are required. An electric unit is submerged in insulating liquid with suitable dielectric and cooling properties. The electric unit is enclosed in a container containing the insulating liquid and gas, such as air, hydrogen gas and etcetera. The container with the submerged electric unit can also be connected to an expansion tank containing insulating liquid and gas. The insulating liquid has a surface comprising an interface between the insulating liquid and the gas.

The value of the relative humidity of the insulating liquid is important for the function of the insulating liquid filled electric apparatus. The relative humidity of the insulating liquid is the ratio between the moisture content and the potential maximum moisture content of the insulating liquid at a certain temperature. Malfunctioning of the insulating liquid filled electric apparatus may occur if the relative humidity of the insulating liquid covering the electric unit is too high. A change in the relative humidity of the insulating liquid has a large influence on the insulating liquid's dielectric withstand. At high relative humidity of the insulating liquid, the insulating liquid's dielectric withstand is low. The insulating liquid's dielectric withstand is also influenced by contamination of particles in the insulating liquid, such a metallic particles from the electrodes of the electric unit. If the insulating liquid's dielectric withstand is low, flashovers in the electric unit may occur, which may damage or limit the function of the electric apparatus.

Based on experience, the insulating liquid of high voltage apparatuses is analyzed and maintained at regular intervals. Samples of insulating liquid can also be taken to measure the amount of moisture in the insulating liquid, for determining the relative humidity of the insulating liquid. The operations to change insulating liquid and take samples of insulating liquid are time consuming and therefore result in higher operating costs of the electric apparatuses. Alternatively a moisture sensor may be positioned in the insulating liquid. However, measurement of moisture in a liquid requires expensive sensors.

Electric apparatuses generate heat when operated, which causes local increase in temperature. This is especially true for tap changers and similar switchgear apparatuses, wherein mechanical contact switches are continuously closed and opened with a high electric potential between the switching points. During switching operation, the insulating liquid can be decomposed into gases, which need to be released. Therefore the container needs to be in communication with an external environment. The external environment is the environment surrounding the insulating liquid filled electric apparatus, such as the air surrounding the container. The communication to the external environment is usually performed through a communication unit, such as a dehydration breather.

The communication unit provides communication between the gas of the container and the external environment. Thereby, gas can pass through the communication unit and the pressure inside the container will be maintained at the pressure of the surrounding environment. When the insulating liquid is heated up, for example by the electric unit, the insulating liquid expands and gas in the container is pressed out to the external environment through the communication unit. Conversely, when the insulating liquid is cooled down, the insulating liquid's volume decreases and gas from the external environment is admitted into the container through the communication unit. Further, the communication unit has the function of providing dehydration of gas passing through the communication unit, that is, the communication unit has the ability to remove moisture of gas passing between the container and the external environment. If the function of the communication unit is poor, the relative humidity in the insulating liquid can increase, which can result in malfunction of the electric apparatuses.

U.S. 20060162304 shows a dehumidifier for oil-insulated electric equipment. A moisture sensor is positioned between the housing of the equipment and a heater in the dehumidifier. Information from the moisture sensor is used for controlling a heater in the dehumidifier. The heater has the function to regenerate the dehumidifier. However, the dehumidifier has no ability to determine the relative humidity in the oil. Further, no means for testing the dehumidifier's ability to remove moisture is disclosed.

SUMMARY OF THE INVENTION

One object of the present invention is to provide a method for determining the relative humidity of an insulating liquid filled electric apparatus.

This object is obtained, by a method that comprises continuously measuring and storing the relative humidity of the gas in the container, calculating an average value of the relative humidity of the gas based on said stored humidity measurements during a certain time period, and determining the relative humidity of the insulating liquid based on said average value of the relative humidity of the gas and a relationship between the relative humidity of the gas and the relative humidity of the insulating liquid at equilibrium.

The relative humidity is a measure of the water content of a substance. The relative humidity of the gas is the ratio between the moisture content and the potential maximum moisture content of the gas at a certain temperature. At equilibrium state in a closed system with gas and insulating liquid, there is equilibrium between the diffusion of water from the gas to the insulating liquid and vice versa. At this equilibrium state, there is a relationship between the relative humidity of the gas and the relative humidity of the insulating liquid. The relationship is temperature-dependent. Due to the communication unit, the insulating liquid filled apparatus is a semi open system that is not in an equilibrium state, and thus said relationship is not valid. However, the changes in the relative humidity of the insulating liquid occur slowly in comparison with the rate of changes in the relative humidity of the gas. An average value of the relative humidity of the gas will be representative of a hypothetical equilibrium state of the container, and is used according to the invention for determining the relative humidity of the insulating liquid. Thus, the relative humidity of the insulating liquid is determined based on said average value of the relative humidity in the gas and said relationship between the relative humidity of the gas and the relative humidity of the insulating liquid at equilibrium.

The average value of the relative humidity is a value that represents a hypothetical equilibrium state of the container. The average value can be calculated based on a plurality of measurement values that have been stored during a time period. Examples on average values are arithmetic mean value, median value, weighted mean value, truncated mean value, or other values that are representative of the relative humidity of a hypothetical equilibrium state. In the same manner an average value of the temperature measurement can be calculated.

The invention has the advantage of determining the relative humidity of the insulating liquid. Hence, procedures such as taking insulating liquid samples or changing insulating liquid according to a maintenance schedule will no longer be necessary, which will reduce the operating cost of the electric apparatus. Further, the invention has the advantage that relative humidity of the insulating liquid can be measured using sensors for measurement of the relative humidity in gas, which have a lower price than moisture sensors for direct measurement of the moisture content in liquid. Thereby, the invention provides a cost-effective determination of the relative humidity of the insulating liquid, which reduces the cost of insulating liquid filled electric apparatuses.

According to an embodiment of the invention, the method further comprises indicating a malfunction of the insulating liquid if the determined relative humidity in the insulating liquid exceeds a certain value. Thereby, it is indicated that the relative humidity of the insulating liquid is higher than desired and there is a risk that the function of the electric apparatus is reduced. When a malfunction of the insulating liquid is indicated the insulating liquid needs to be dried or changed to new insulating liquid with sufficiently low relative humidity.

According to an embodiment of the invention, the method further comprises: continuously measuring and storing the temperature of the insulating liquid of the container, calculating an average value of the temperature in the container based on said stored temperature measurements during said time period, producing a relationship between the relative humidity of the gas and the relative humidity of the insulating liquid at equilibrium in dependence on the average value of the temperature, and determining the relative humidity of the insulating liquid based on the produced relationship.

By producing a relationship between the relative humidity of the gas and the relative humidity of the insulating liquid, the average value of the temperature in the container is used for either selecting or calculating the relationship. Thereby, a more accurate value of the relative humidity in the insulating liquid can be determined.

According to an embodiment of the invention, the method further comprises determining the average value of the relative humidity based on stored humidity measurements during a time period of more than one day, and preferably 2-3 days. Because the changes in the relative humidity of the insulating liquid occur slowly in comparison with the changes in the relative humidity of the gas, a calculated average value of the relative humidity during a time period of more than one day capture the variation in the relative humidity of the gas. Thus, a more accurate value of the relative humidity in the insulating liquid can be determined.

Another object of the invention is to indicate a malfunction of an insulating liquid filled electric apparatus. This object is accomplished with a method comprising indicating a malfunction of the insulating liquid and indicating a malfunction of the communication unit. By using a combination of these two malfunctions, a reliable diagnosis of both the current and the future status of the electric apparatus is indicated. This results in a safe operation of the electric apparatus. yet According to an embodiment of the invention, the method further comprises: detecting when the temperature in the insulating liquid drops between a first and a second temperature, and the difference between the first and the second temperature is larger than a certain value, calculating the difference in the relative humidity of the gas in the container at the first temperature and at the second temperature, and indicating a malfunction of the communication unit based on said calculated relative humidity difference.

At a temperature drop the insulating liquid is cooled down, and thus the density of the insulating liquid increases and the volume of the insulating liquid decreases. To maintain the same pressure within the container as the pressure of the external environment, gas from the external environment is admitted into the container through the communication unit. At a detected temperature drop, the relative humidity of the gas that is admitted into the container through the communication unit is to be reduced by means of the dehydration function of the communication unit. Thus, a functioning communication unit shall reduce the relative humidity of the gas passing through the communication unit. If the communication unit has no reduction or poor reduction of the relative humidity of the gas passing through the communication unit, there is a malfunctioning of the communication unit.

A malfunction of the communication unit is indicated, based on the calculated difference in the relative humidity at the first temperature and the second temperature. Preferably, the method further comprises indicating a malfunction of the communication unit when the calculated difference in the relative humidity at the first temperature and the second temperature is less than a certain value. At a malfunction of the communication unit, the ability of the communication unit to reduce the relative humidity from gas passing through the communication unit is lower than desired. Thereby, it is possible that the relative humidity of the insulating liquid of container will increases above a level that puts the function of the electric apparatus at risk. The embodiment makes it possible to indicate a malfunction of the communication unit, and thereby the safe operation of the electric apparatus can be assured.

Another object of the present invention is to provide a device for determining the relative humidity of an insulating liquid filled electric apparatus.

This object is obtained by a device comprising a second sensor configured to continuously measure the relative humidity of the gas in the container, a computing unit configured to receive and store measurement values from the second sensor, and to calculate an average value of the relative humidity in the gas based on said stored humidity measurements during a certain time period, to determine the relative humidity of the insulating liquid based on said average value of the relative humidity in the gas and a relationship between the relative humidity of the gas and the relative humidity of the insulating liquid at equilibrium.

The computing unit is a device with the function of storing and processing measurement data. Based on the processed data and the relationship between the relative humidity of the gas and the relative humidity of the insulating liquid at equilibrium, malfunctioning of insulating liquid filled apparatus can be indicated.

The method and device according to the invention is advantageously used for detecting a malfunction of a tap changer.

A tap changer is an electric apparatus with connection point along a transformer winding. Thereby, the number of turns on the transformer winding can be controlled with the purpose of enabling voltage regulation of the secondary side. A tap changer is an electric apparatus that is submerged in insulating liquid for the purpose of isolation and cooling.

BRIEF DESCRIPTION OF THE DRAWINGS

The invention will now be explained more closely by the description of different embodiments of the invention and with reference to the appended figures.

DETAILED DESCRIPTION OF THE INVENTION

Figure 1A:
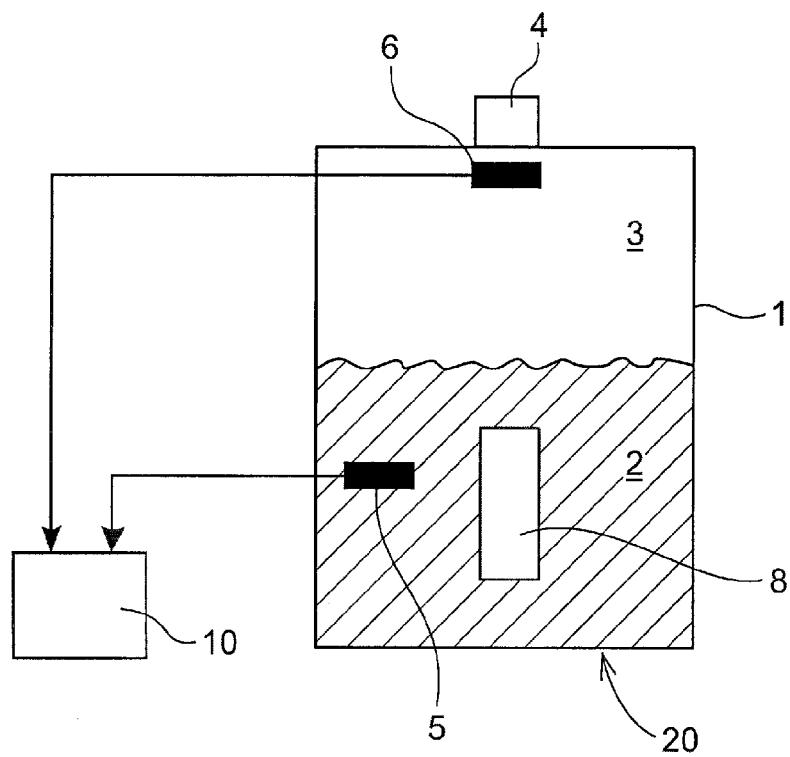
FIG. 1a shows an example of an insulating liquid filled apparatus including a device according to an embodiment of the invention.

FIG. 1a shows an example of an insulating liquid filled apparatus 20 including a device for detecting malfunction of the apparatus according to an embodiment of the invention. The insulating liquid filled apparatus 20 includes a container 1 containing insulating liquid 2 and gas 3. The insulating liquid 2 has suitable dielectric and cooling properties. The insulating liquid 2 has a surface forming an interface between the insulating liquid 2 and the gas 3. The insulating liquid filled apparatus 20 further includes an electric unit 8, such as a tap changer, which is enclosed within the container 1 and is completely submerged in the insulating liquid 2. The electric unit 8 performs operation in which heat is produced and where the insulating liquid 2 can be decomposed into gases. The insulating liquid filled apparatus 20 is provided with a communication unit 4, such as a dehydration breather, which is positioned at the rim of the container 1. The communication unit 4 provides communication between the gas 3 of the container and gas surrounding the insulating liquid filled electric apparatus 20. Thereby, gases produced within the insulating liquid filled apparatus 20 can be released and the pressure of the gas 3 is maintained at the same pressure as the gas surrounding the insulating liquid filled apparatus 20. The communication unit 4 furthermore has the function of providing dehydration of gas passing through the communication unit 4. Thereby, it is ensured that the relative humidity of the gas 3 within the container 1 is sufficiently low so that likewise the relative humidity of the insulating liquid 2 within the container 1 will be maintained at a low level.

FIG. 1a also shows an example of a device for detecting malfunction of the apparatus 20 of an embodiment of the invention. The device in FIG. 1a has the function of providing detection of malfunctioning of insulating liquid filled electric apparatus 20. The device is capable of detecting two separate malfunctions, firstly a malfunction of the insulating liquid 2, and secondly a malfunction of the communication unit 4. The malfunction of the insulating liquid 2 is indicated when the relative humidity of the insulating liquid 2 exceeds a certain value, where the isolation and cooling properties of the insulating liquid 2 are reduced so that the function of the insulating liquid filled apparatus 20 is at risk. The malfunction of the communication unit 4 is indicated when the dehydration function of gas passing through the communication unit 4 is reduced, so that there is a risk that the relative humidity of the insulating liquid 2 will increase.

The device for detecting malfunction of the apparatus shown in FIG. 1a comprises a temperature sensor 5 and a relative humidity sensor 6. The temperature sensor 5 is configured to continuously measure the temperature of the insulating liquid in the container 1. In the shown embodiment, the temperature sensor 5 is positioned in the liquid 2 within the container 1. The temperature sensor 5 can for example be a thermistor, a thermocouple or any other sensor that enables continuous measurement of temperature. The relative humidity sensor 6 is configured to continuously measure the relative humidity of the gas 3 in the container 1. The relative humidity sensor 6 is positioned in the gas 3 within the container 1 at a distance from the surface of the insulating liquid 2. In a preferable example, the humidity sensor 6 is positioned close to the communication unit 4. The relative humidity sensor 6 may for example be a capacitive polymer sensor or any other sensor that enables continuous measurement of the relative humidity in different gases.

Figure 1B:
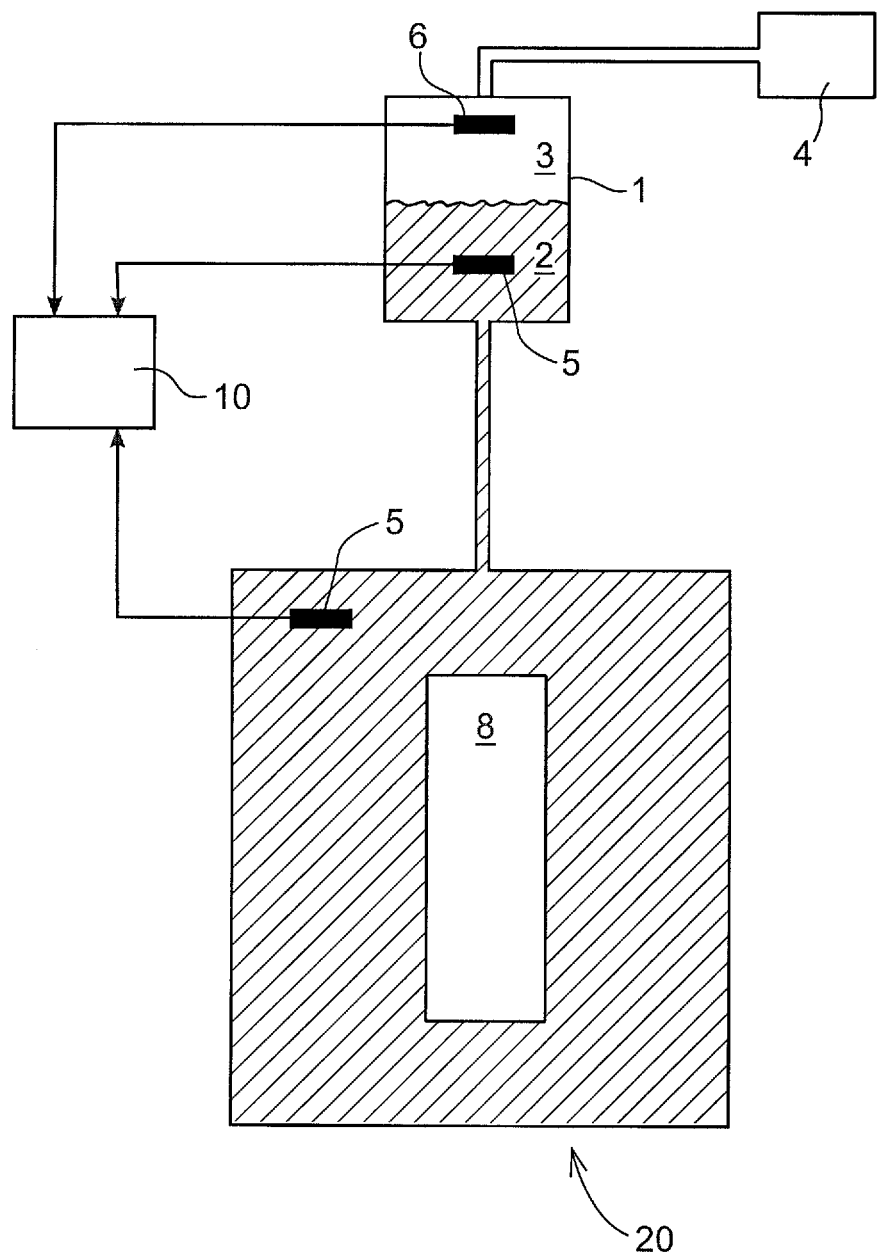
FIG. 1b shows an example of an insulating liquid filled apparatus connected to an expansion tank.

FIG. 1b shows an insulating liquid filled apparatus 20, where the container 1 comprises a main container, including the electric unit 8, and an expansion tank, including the intersection between the insulation liquid 2 and the gas 3. Thereby, it can be assured that the electric unit 8 is always submerged in the insulating liquid 2. In the shown example, the temperature is measured at several positions in the container, such as in the main container and in the expansion tank. Thereby, a temperature change within the insulating liquid representative to the whole container can be determined.

The device for detecting malfunction of the apparatus further comprises a computing unit 10, positioned outside the insulating liquid filled electric apparatus 20. The computing unit comprises a processor, such as a Central Processing Unit (CPU), and a storage media, such as Random Access Memory (RAM) or other types of storage media. The computing unit 10 is configured to receive and store measurement values from the temperature sensor 5 and the relative humidity sensor 6.

The computing unit 10 is further configured to perform several tasks wherein the stored measurement values are processed. The processed measurement values are used by the computing unit 10 for performing tasks where malfunctions of the insulating liquid filled electric apparatus 20 are detected and indicated.

Figure 3:
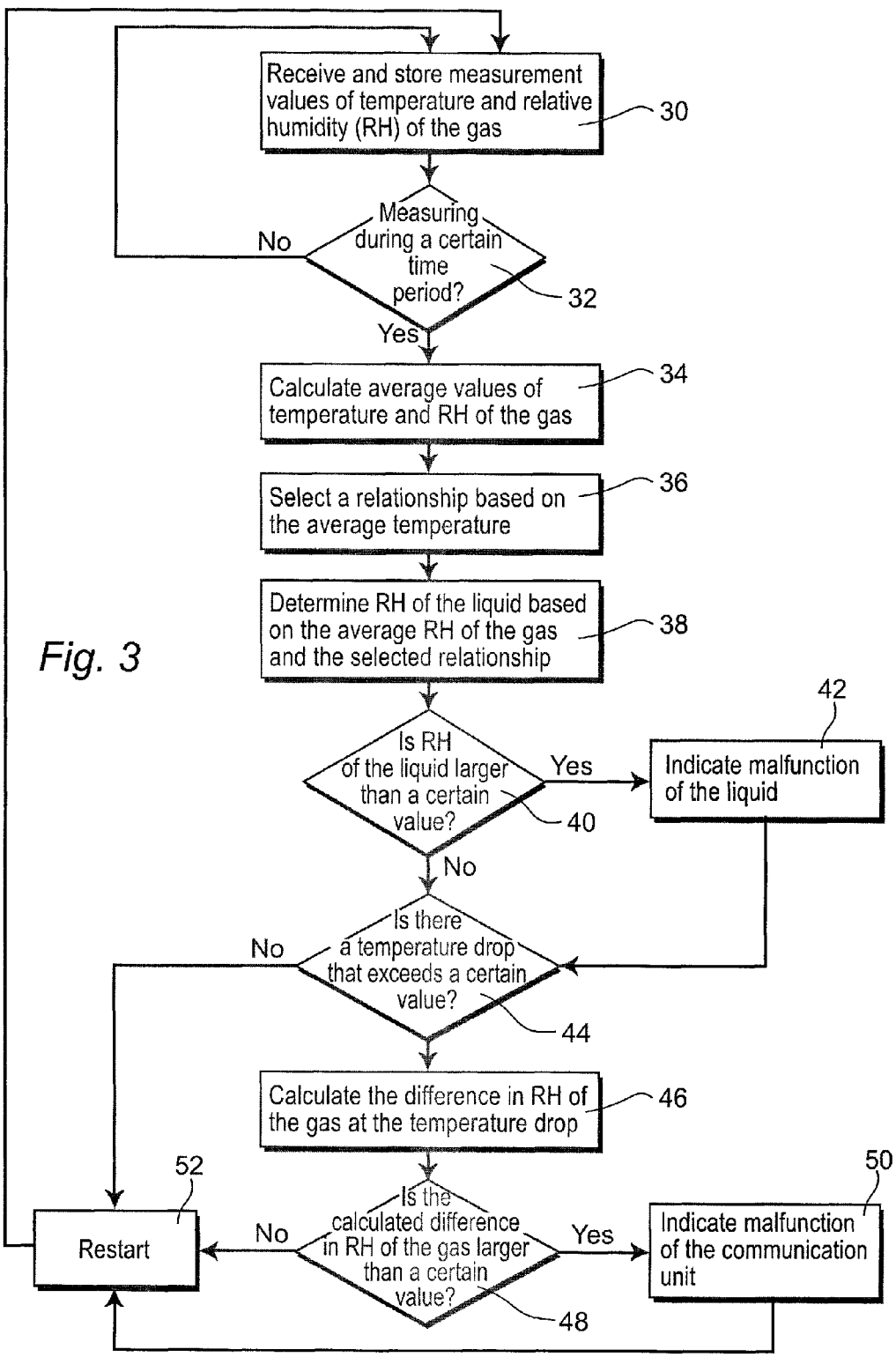
FIG. 3 shows a flow diagram of a method according to an embodiment of the invention.

The main task of the computing unit 10 is to execute the methods as defined in the claims according to the invention. FIG. 3 is a flowchart illustration of a method and computer program product according to an embodiment of the present invention. It will be understood that each block of the flowchart can be implemented by computer program instructions. In a first step of the method, measurement values of temperature and relative humidity (RH) from the temperature sensor 5 and the relative humidity sensor 6 are received and stored, block 30. If the measurements have been performed within less than a certain time period, more measurement values need to be receive and store before proceeding in the method, block 32. The measurement values will be stored within a certain time-window, so that measurement values older than a certain value will be excluded from the method. The duration of the time period is preferably long enough to capture the variation in temperature and relative humidity during the operation of the insulating liquid filled electric apparatus 20, such as 2-3 days.

In the following part of the method as shown in FIG. 3, an average value of the relative humidity of the gas 3 and the temperature in the container 1 is calculated based on stored measurement values, block 34. Examples on average values are arithmetic mean value, median value, or other types of average values. The average value of the relative humidity of the gas will be representative of a hypothetical equilibrium state of the container 1. The average temperature is used for selecting a relationship between the relative humidity of the gas and the relative humidity of the insulating liquid 2 at equilibrium, further denoted the relationship. The relationship is selected from a number of stored relationships, block 36. Alternatively, the relationship can be calculated based on the average temperature. Thereby, a more accurate value of the relative humidity of the insulating liquid can be determined.

Figure 2:
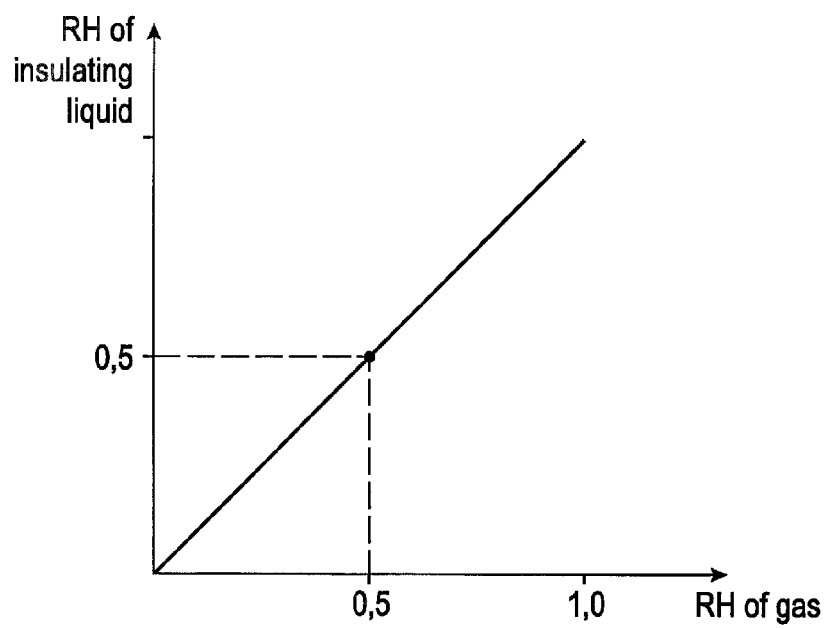
FIG. 2 shows an example of the relationship between the relative humidity of the gas and the relative humidity of the insulating liquid at equilibrium at a certain temperature.

FIG. 2 shows an example of a relationship between the relative humidity of the gas 3 and the relative humidity of the insulating liquid 2 at equilibrium at a certain temperature. On the x-axis the relative humidity of the gas 3 is shown. On the y-axis is the relative humidity of the insulating liquid 2 is presented. This relationship is temperature-dependent. The relationship displays an equilibrium state between the diffusion of water from the gas 3 to the insulating liquid 2 and vice versa. Because the changes in the relative humidity of the insulating liquid 2 occurs slowly in comparison with the rate of changes in the relative humidity of the gas 3, an average value of the relative humidity of the gas 3 will be representative of a hypothetical equilibrium state of the container 1. Thereby, the relationship shown in FIG. 2 can be used together with a calculated average value of the relative humidity of the gas 3, to determine the relative humidity in the insulating liquid 2.

For example, using the shown relationship in FIG. 2 and assuming average value of the relative humidity of the gas 3 has been calculated at 0.5. From the relationship the relative humidity in the insulating liquid 2 can be determined at the same relative humidity value, namely 0.5.

In the next part of the method shown in FIG. 3, the relative humidity of the insulating liquid (RH) is determined based on the average value of the relative humidity in the gas 3 and the selected relationship, block 38. If the determined relative humidity of the insulating liquid is larger than certain value, a malfunction of the insulating liquid 2 is indicated, block 42. Thereby, for example an alarm is produced or the insulating liquid filled electric apparatus 20 is stopped and the insulating liquid 2 can be replaced with insulating liquid containing low relative humidity.

In case the relative humidity of the insulating liquid does not exceed certain value, the ability of the communication unit 4 to reduce the relative humidity from gas passing through the communication unit 4 is tested by the method as shown in FIG. 3. This test can be performed in case there is a temperature drop that exceeds a certain value, block 44. In case no such temperature drop is detected, the method is ended, block 52. At a detected temperature drop larger than a certain value, gas from the external environment is taken into the container 1. The difference in the relative humidity of the gas 3 in the container at the temperature drop is calculated, block 46. If the calculated difference in relative humidity exceeds a certain value, a malfunction of the communication unit 4 is indicated, block 50. Otherwise, the method is restarted, block 52. Thus, the liquid filled electric apparatus 20 can be monitored during its operation.

The present invention is not limited to the embodiments disclosed but may be varied and modified within the scope of the following claims. For example the invention may exclusively be provided with the ability to indicate a malfunction of the insulating liquid 2. The relative humidity does not need to exceed a certain level to be indicated: alternatively the determined relative humidity of the insulating liquid 2 can be presented separately.

The invention claimed is:

1. A method for determining the relative humidity of an insulating liquid filled electric apparatus, the method comprising the steps of:
   providing a container containing insulating liquid and gas, a communication unit providing communication between the gas of the container and gas of an external environment, and dehydration of gas passing through the communication unit:
   providing an electric unit and enclosing the electric unit within the container such that the electric unit is completely submerged within the liquid and below an interface between the liquid and the gas of the container;
   continuously measuring by a sensor and storing by a computing unit a measurement of the relative humidity of the gas in the container,
   calculating by the computing unit an average value of the relative humidity of the gas based on said stored humidity measurements during a certain time period, and
   determining by the computing unit the relative humidity of the insulating liquid based on said average value of the relative humidity of the gas and a relationship between the relative humidity of the gas and the relative humidity of the insulating liquid at equilibrium.

2. The method according to claim 1, wherein the method further comprises indicating a malfunction of the insulating liquid if said determined relative humidity of the insulating liquid exceeds a certain value.

3. The method according to claim 1, wherein the method further comprises:
   continuously measuring and storing the temperature of the insulating liquid of the container,
   calculating an average value of the temperature in the container based on said stored temperature measurements during said time period,
   producing a relationship between the relative humidity of the gas and the relative humidity of the insulating liquid at equilibrium in dependence on the average value of the temperature, and
   determining the relative humidity of the insulating liquid based on the produced relationship.

4. The method according to claim 1, wherein the average value of the relative humidity is based on stored humidity measurements during a time period of more than one day.

5. The method according to claim 1, wherein the method further comprises:
   detecting when the temperature in the insulating liquid drops between a first and a second temperature, and the difference between the first and the second temperature is larger than a certain value,
   calculating the difference in the relative humidity of the gas in the container at the first temperature and at the second temperature, and
   indicating a malfunction of the communication unit based on said calculated relative humidity difference.

6. The method according to claim 5, wherein the malfunction of the communication unit is indicated when said calculated relative humidity difference is less than a certain value.

7. The method according to claim 1, wherein the electric unit is a tap changer and wherein such method detects a malfunction of the tap changer.

8. A device for determining the relative humidity of an insulating liquid filled electric apparatus, the device comprising:
- a container containing insulating liquid and gas;
- a communication unit providing communication between the gas of the container and gas of an external environment, and providing dehydration of gas passing through the communication unit;
- an electric unit enclosed within the container, the electric unit being completely submerged within the liquid and below an interface between the liquid and the gas of the container;
- a first sensor is configured to continuously measure the temperature in the insulating liquid of the container;
- a second sensor configured to continuously measure the relative humidity of the gas;
- a computing unit configured to receive and store measurement values from the second sensor, and to calculate an average value of the relative humidity in the gas based on said stored humidity measurements during a certain time period, to determine the relative humidity of the insulating liquid based on said average value of the relative humidity of the gas and a relationship between the relative humidity of the gas and the relative humidity of the insulating liquid at equilibrium.

9. The device according to claim 8, wherein the computing unit is configured to indicate a malfunction of the insulating liquid if said determined relative humidity of the insulating liquid exceeds a certain value.

10. The device according to claim 8, wherein the computing unit is configured to receive and store measurement values from the first sensor and the second sensor, and to calculate an average value of the temperature in the container based on said stored temperature measurements during a certain time period, and to produce a relationship between the relative humidity of the gas and the relative humidity of the insulating liquid at equilibrium in dependence on the average value of the temperature, and to determine the relative humidity of the insulating liquid based on said average value of the relative humidity in the gas and the produced relationship between the relative humidity of the gas and the relative humidity of the insulating liquid at equilibrium.

11. The device according to claim 8, wherein the computing unit is configured to receive and store measurement values from the first sensor and the second sensor, to detect when the temperature in the insulating liquid drops between a first and a second temperature, and the difference between the first and the second temperature is larger than a certain value, to calculate the difference in the relative humidity of the gas in the container at the first temperature and at the second temperature, and to indicate a malfunction of the communication unit based on said calculated humidity difference.

12. The device according to claim 8, wherein the electric unit is a tap changer.

* * * * *